United States Patent [19]

Ogawa et al.

[11] Patent Number: 4,714,765
[45] Date of Patent: Dec. 22, 1987

[54] RHODANINE DERIVATIVES AND PROCESS FOR PREPARING THE SAME

[75] Inventors: Kazuo Ogawa; Takaji Honna, both of Tokushima, Japan

[73] Assignee: Taiho Pharmaceutical Company, Limited, Tokyo, Japan

[21] Appl. No.: 810,594

[22] Filed: Dec. 19, 1985

[30] Foreign Application Priority Data

Jul. 10, 1985 [JP] Japan .................. 60-152632

[51] Int. Cl.⁴ .......................................... C07D 417/06
[52] U.S. Cl. .................................................. 548/183
[58] Field of Search ........................................ 548/183

[56] References Cited

FOREIGN PATENT DOCUMENTS

| | | | |
|---|---|---|---|
| 47109 | 3/1982 | European Pat. Off. ............. | 548/183 |
| 54-30171 | 6/1979 | Japan .................................... | 548/183 |
| 61-27984 | 2/1986 | Japan .................................... | 548/183 |
| 62-10993 | 10/1987 | Japan .................................... | 548/183 |
| 489335 | 7/1938 | United Kingdom ................ | 548/183 |
| 467058 | 9/1972 | U.S.S.R. .............................. | 548/183 |

*Primary Examiner*—Robert Gerstl
*Attorney, Agent, or Firm*—Murray and Whisenhunt

[57] ABSTRACT

Disclosed are a compound of the formula

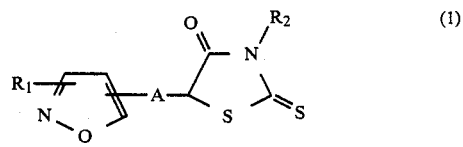

wherein $R_1$ is lower alkyl, A is a group of the formula

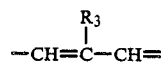

(in which $R_3$ is hydrogen or lower alkyl) or methylene, and $R_2$ is hydrogen or a group of the formula $-(CH_2)_n COOH$ (in which n is an integer of 1 to 6) or a salt of the derivative, and preparation thereof. The compounds have an excellent aldose reductase inhibitory action.

9 Claims, No Drawings

RHODANINE DERIVATIVES AND PROCESS FOR PREPARING THE SAME

This invention relates to novel rhodanine derivatives and process for preparing the same, and more particularly to novel rhodanine derivatives useful for preventing or treating complications due to aldose reductase and process for preparing such rhodanine derivatives.

A variety of compounds have been developed for treating diabetes caused by the increase of blood sugar resulting from the decrease of insulin secreted from the pancreas. No compound, however, is known which is sufficiently effective in preventing or treating complications developing due to aldose reductase in the course of chronic diabetes, such as diabetic cataract, neuropathy and nephropathy.

Medicaments having a rhodanine skeletone for treating such complications are known, e.g. those disclosed in Japanese Unexamined Patent Publications No. 28074/1982 and No. 40478/1982 but they are unsatisfactory in their efficacy.

An object of the invention is to provide a class of compounds which are sufficiently effective for preventing or treating the complications due to aldose reductase.

Another object of the invention is to provide a process for preparing such compounds.

These objects and other features of the invention will become apparent from the following description.

The present invention provides compounds of the formula

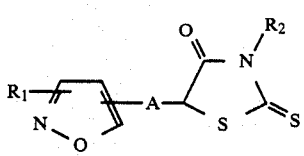

(1)

wherein $R_1$ is lower alkyl, A is a group of the formula

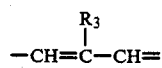

(in which $R_3$ is hydrogen or lower alkyl) or methylene, and $R_2$ is hydrogen or a group of the formula $-(CH_2)_nCOOH$ (in which n is an integer of 1 to 6) or salts of the derivatives.

We conducted extensive research to develop compounds having a high aldose reductase inhibitory activity and found that the rhodanine derivatives of the formula (1) and salts thereof exhibit outstanding action of inhibiting aldose reductase, and further show excellent actions of lowering blood sugar level and also decreasing the level of lipids. This invention has been accomplished based on this novel finding.

The compounds of the invention are novel compound undisclosed in literature. The compounds of the invention have the foregoing excellent actions of inhibiting aldose reductase, and of lowering blood sugar level and lipid level, and therefore are useful as a medicament for treating complications due to aldose reductase and also for treating diabetes and related diseases.

A preferred class of the compounds of the invention consists of those represented by the formula

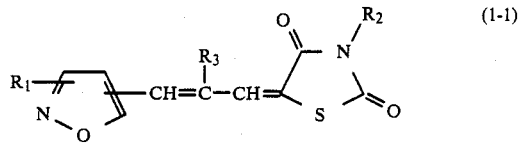

(1-1)

wherein $R_1$, $R_2$ and $R_3$ are as defined above.

Another preferred class of the compounds of the invention consists of those represented by the formula

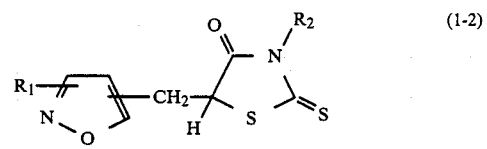

(1-2)

wherein $R_1$ is as defined above, and $R_2$ is as defined above, or preferably a group $-CH_2COOH$.

Examples of lower alkyl groups represented by $R_1$ and $R_3$ in the formula (1) are straight chain or branched chain $C_1-C_6$ alkyl groups such as methyl, ethyl, propyl, isopropyl, butyl, sec-butyl, tert-butyl, iso-butyl, pentyl, sec-pentyl, hexyl, etc. The salts of the compounds according to this invention can be formed only from those in which $R_2$ is a group $-(CH_2)_nCOOH$, and include all the salts formed by the reaction of the carboxylic acid represented by the group $-(CH_2)_nCOOH$ with a base, preferably a base which forms a pharmaceutically acceptable salt. Such salts include salts with alkali metals such as sodium, potassium and lithium; alkaline earth metals such as calcium and magnesium; ammonium; tetra($C_1-C_4$ alkyl)ammonium such as tetramethylammonium, tetraethylammonium, tetrapropylammonium and tetrabutylammonium; and salts with organic amines including mono- and di-($C_1-C_4$ alkyl)amines such as methylamine, ethylamine, isopropylamine, tert-butylamine, dimethylamine and diethylamine; $C_5-C_7$ cycloalkylamines such as cyclopentylamine and cyclohexylamine; phenyl-$C_1-C_3$-alkylamines such as benzylamine, phenethylamine and phenylpropylamine; 5- or 6-membered heterocyclic compounds containing in its ring structure one or two nitrogen atoms as the heteroatom, such as piperidine, piperazine, imidazoline and pyrrole; mono- or di-($C_1-C_4$ alkanol)amines such as monoethanolamine, monopropanolamine and diethanolamine; basic amino acids such as lysine, arginine and hystidine; etc.

These salts can be prepared from the compound of the formula (1) in which $R_2$ is $-(CH_2)_nCOOH$ by a conventional process, for example by reacting the compound of the formula (1) with a theoretical amount of a suitable base in an appropriate solvent. Examples of useful bases are hydroxides or carbonates of alkali metals and alkaline earth metals, ammonium hydroxide, ammonia, tetra ($C_1-C_4$ alkyl)ammonium halides, or the organic amines exemplified above, etc. Useful solvents include $C_1-C_6$ monohydric alkanols such as methanol and ethanol, acetone, dimethylformamide, water, a mixture of $C_1-C_6$ monohydric alkanol and water, etc. The salt can be separated by lyophilizing the solution when soluble in the solvent used, or by filtering the reaction mixture when insoluble or sparingly soluble in the solvent used, if required after distilling off the solvent.

The rhodanine derivatives of the formula (1) according to this invention can be prepared, for example, by the process as shown below in Reaction Scheme I.

REACTION SCHEME I

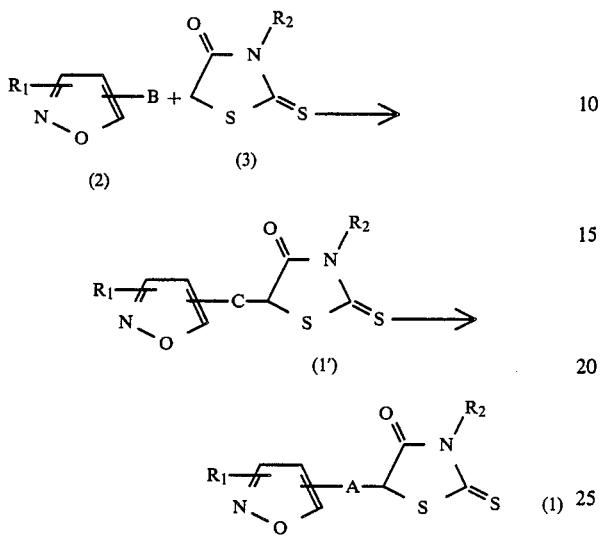

In the foregoing formulas, $R_1$, $R_2$ and A are as defined above, B is a group of the formula $-CH=C(R_3)-CHO$ (in which $R_3$ is as defined above) or $-CHO$ and C is a group of the formula $-CH=C(R_3)-CH=$ (in which $R_3$ is as defined above) or $-CH=$.

According to Reaction Scheme I, the condensation is conducted between the aldehyde compound of the formula (2) and the compound of the formula (3) under the conventional conditions for aldol condensation or Knoevenagel condensation to give the compound of the formula (1'). Of the compounds of the formula (1'), those wherein C is $-CH=$ are subsequently reduced to obtain the compound of the formula (1-2) in accordance with this invention.

The aldol condensation and Knoevenagel condensation are well known, and are described, for example, in Merck Index, 10th Edition, "Organic name reactions". Examples of solvents useful in the condensation are $C_1-C_4$ aliphatic alcohols such as ethanol, methanol and isopropanol, $C_1-C_3$ alkanoic acids such as acetic acid, anhydrides of the alkanoic acids such as acetic anhydride, propionic anhydride, di($C_1-C_4$ alkyl)ethers such as diethyl ether and dipropyl ether, cyclic ethers such as tetrahydrofuran, dioxane and the like. Examples of catalysts useful in the condensation are basic compounds which are conventionally used for aldol condensation or Knoevenagel condensation. Examples of such basic compounds serving as the catalyst are inorganic bases including hydroxides, carbonates, hydrogencarbonates, $C_1-C_6$ alkoxides and $C_1-C_6$ alkanoic acid salts of alkali metals and alkaline earth metals, such as potassium hydroxide, sodium hydroxide, calcium hydroxide, sodium carbonate, sodium hydrogencarbonate, sodium methoxide, sodium ethoxide, magnesium ethoxide and sodium acetate, and ammonia; and organic bases including mono-, di- and tri-($C_1-C_4$ alkyl)amines such as methylamine, ethylamine, diethylamine, triethylamine, aniline, nicotine, pyridine, piperidine and the like. Although the amounts of the aldehyde derivative of the formula (2) and the compound of the formula (3) are suitably determined, it is preferred to use the compound of the formula (3) in an amount of about 1.0 to about 1.2 moles per mole of the aldehyde derivative of the formula (2). The catalyst is used in a conventional amount of about 0.1 to about 1.0 mole per mole of the compound of the formula (2). The reaction is usually performed with heating and advantageously proceeds as a rule at a temperature of about 50 to about 150° C., preferably at the reflux temperature of the solvent, and completed in about 1 to about 10 hours. The foregoing reaction gives a compound of the formula (1') wherein C is a group of the formula $-CH=C(R_3)-CH=$ wherein $R_3$ is as defined above, i.e., a compound of the formula (1) wherein A is a group of the formula $-CH=C(R_3)-CH=$ wherein $R_3$ is as defined above.

The resulting compound of the formula (1') wherein C is $-CH=$ is further subjected to a reduction. The reduction is conducted usually in liquid phase under a hydrogen pressure of between atmospheric pressure and about 10 atm. The solvents to be used in the reduction are not specifically limited unless they adversely affect the reaction, and include water, methanol, ethanol, acetone and the like. Water is usually preferred. When the compound of the formula (1') is insoluble or sparingly soluble in water, it is preferred to transform the compound (1') into a water-soluble salt of alkali metal such as sodium, potassium or the like prior to reduction. While the reduction is more advantageously effected with the increase in hydrogen pressure, the reaction sufficiently proceeds under a hydrogen pressure of between about atmospheric pressure to about 10 atm. The temperature is suitably determined, but ranges generally from about 10 to about 50° C., preferably around room temperature. Useful catalysts include those effective for hydrogenating the C-C double bond, such as platinum, palladium, nickel and the like. The foregoing reaction gives the compound of the invention in which A is methylene. The reduction is usually completed in about 1 to about 10 hours.

The compound of the formula (1) of the invention prepared by the aforesaid process can be easily separated from the reaction product by conventional separation methods such as column chromatography, recrystallization method, etc.

The compounds of the formula (3) and the compounds of the formula (2) wherein B is $-CHO$ are known or can be prepared by known methods. The aldehyde compounds of the formula (2) serving as the starting material in which B is a group $-CH=C(R_3)-CHO$, i.e. compounds of the formula (2'), are novel substances and can be produced; for example, by the process as shown below in Reaction Scheme II.

REACTION SCHEME II

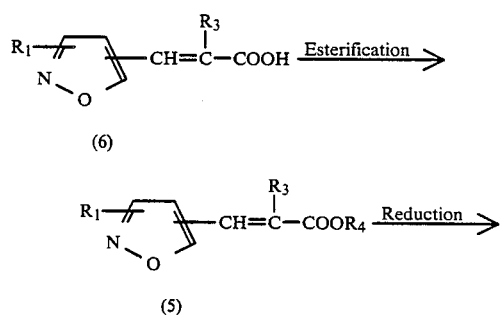

-continued

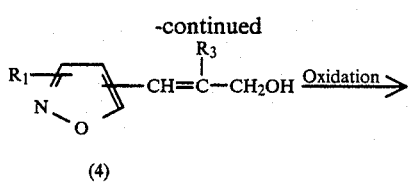

(4)

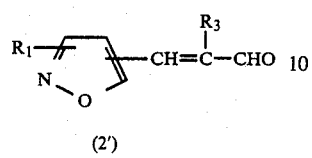

(2')

In the foregoing formulas, $R_1$ and $R_3$ are as defined above and $R_4$ is lower alkyl, such as $C_1$-$C_6$ alkyl.

The acrylic acid derivative of the formula (6), which is a known compound and can be prepared by a known process, is esterified with e.g. a lower alkanol-sulfuric acid mixture into the ester derivative of the formula (5), which is reduced with e.g. di-isobutyl aluminum hydride to give the alcohol derivative of the formula (4). Subsequently the derivative of the formula (4) is oxidized with e.g. pyridinium chlorochromate to produce the acrylaldehyde derivative of the formula (2'). The foregoing processes for preparing the starting material will be described in detail in Reference Examples below.

For use in preventing or treating the diseases caused by aldose reductase, e.g. diabetic cataract, neuropathy and nephropathy or in preventing or treating diabetes, the rhodanine derivatives of the present invention are administered to mammals including humans in pharmaceutical dosage form such as oral preparation, injection, rectal suppository or eye drop, in accordance with the purpose of therapy contemplated. Such preparations can be formulated in the manner already known in the art, using conventional pharmaceutically acceptable, non-toxic carriers or excipients. For the formulation of solid preparations for oral administration, such as tablets, coated tablets, granules, powders and capsules, excipients and, when required, binders, disintegrators, lubricants or glazes, coloring agents, corrigents, etc. can be added to the compound of this invention. Such additives are already known in the art and useful examples are excipients such as lactose, white sugar, sodium chloride, glucose solution, starch, calcium carbonate, kaolin, crystalline cellulose and silicic acid; binders such as water, ethanol, propanol, glucose, carboxymethyl cellulose, shellac, methyl cellulose, potassium phosphate and polyvinyl pyrrolidone; disintegrators such as dried starch, sodium alginate, agar powder, sodium hydrogencarbonate, calcium carbonate, sodium lauryl sulfate, glyceryl monostearate, starch and lactose; lubricants or glazes such as purified talc, stearic acid salt, boric acid powder, solid polyethylene glycol; corrigents such as sucrose compound bitter orange peel, citric acid, tartaric acid, etc. For the formulation of liquid preparations for oral administration, such as solutions for oral administration, syrups, etc., conventional corrigents, buffers, stabilizers, etc. can be added to the compound of the invention. Such preparations can be formulated in the usual manner. Examples of useful corrigents are those exemplified above. Typical buffers include sodium citrate. Stabilizers include tragacanth, gum arabic, gelatin, etc. The pharmacological compositions thus prepared are orally administered. Parenteral solutions can be formulated in the usual manner using distilled water for injection as the carrier and adding to the compound of the invention conventional additives such as pH-adjusting agents, buffers, stabilizers, isotonic agents, local anesthetics, etc. Examples of the pH-adjusting agents and buffers are sodium salts of citric acid, acetic acid and phosphoric acid. The stabilizers include sodium pyrosulfite (anti-oxidant), EDTA, thioglycolic acid, thiolactic acid, etc. Examples of useful local anesthetics are procaine hydrochloride, xylocaine hydrochloride, lidocaine hydrochloride, etc. Such solutions can be given subcutaneously, intramuscularly or intravenously. For the preparation of rectal suppositories, conventional excipients such as fatty acid triglyceride and like base and if required, Tween and like sufactants, etc. can be added to the compound of the invention, followed by formulation in the usual manner. Such suppositories are administered to the rectum. For the preparation of eye drops, conventional diluents such as sterilized distilled water, phisiological saline, etc. can be used. Eye drops should preferably be made isotonic to tears by using a conventional pH-adjusting agent, buffers, etc.

The amount of the compound of the invention to be incorporated into the preparations varies with the symptoms of the patient or with the type of the preparation. Preferably the amount per administration unit is about 10 to about 300 mg for oral administration, about 10 to about 50 mg for parenteral administration, about 10 to about 200 mg for intrarectal administration, and about 5 to about 50 mg for administration to the eyes. The compound of the present invention is administered to the patient in an effective amount for inhibiting aldose reductase or for treating diabetes. The effective amount is suitably decided in accordance with the knowledge of the medical art. The dosage per day for an adult, which is variable with the symptoms, age, sex and the like, is preferably about 5 to about 900 mg/kg of body weight for usual purposes.

The present invention will be described below in more detail with reference to the following Examples.

Reference Example 1

A 8 g quantity of 3-methylisoxazole-5-acrylic acid was added to 300 ml of methanol and 20 ml of concentrated sulfuric acid and the mixture was refluxed with heating for 6 hours. After completion of the reaction, the solvent was removed by distillation. Ice water was added to the residue and the precipitated crystals were separated by filtration and recrystallized from methanol, giving 8 g of methyl 3-methyl-5-isoxazolyl-acrylate (Compound 5a) having a melting point of 99 to 100° C. in a yield of 91.6 %.

Elementary analysis (for $C_8H_9NO_3$):

|  | C | H | N |
|---|---|---|---|
| Calcd. (%) | 57.48 | 5.43 | 8.38 |
| Found (%) | 57.97 | 5.58 | 8.46 |

REFERENCE EXAMPLE 2

Compounds 5b and 5c as shown below in Table 1 were prepared in the same manner as in reference Example 1.

TABLE 1

$$R_1\underset{N\diagdown O}{\overset{R_3}{\diagup\hspace{-0.3em}\diagdown}}CH=\overset{R_3}{\underset{|}{C}}-CO_2CH_3 \quad (5)$$

| Comp. No. | $R_1$ | Position of methyl arylate | $R_3$ | Yield (%) | mp (°C.) | Molecular formula |
|---|---|---|---|---|---|---|
| 5a | 3-$CH_3$ | 5 | H | 91.6 | 99–100 | $C_8H_9NO_3$ |
| 5b | 5-$CH_3$ | 3 | H | 82.5 | 98–99 | $C_8H_9NO_3$ |
| 5c | 3-$CH_3$ | 5 | $CH_3$ | 83.1 | 57–59 | $C_9H_{11}NO_3$ |

REFERENCE EXAMPLE 3

A 8 g quantity of methyl 3-methyl-5-isoxazolylacrylate was dissolved in 150 ml of dichloromethane. To the solution was added dropwise with cooling at −70° C. or lower 100 ml of a 25 % solution of di-isobutyl aluminum hydride in toluene. After the addition, the reaction was effected for 30 minutes and then the excess of the reducing agent was decomposed with methanol-water. The organic layer was separated and dried over anhydrous sodium sulfate. After drying, the solvent was removed by distillation, giving 4.5 g of 3-methyl-5-isoxazolyl-allyl alcohol (Compound 4a) as an oil in a yield of 67.6 %. MS, m/e : 139 (M+).

$^1$H-NMR, δ(ppm) : 2.30 (3H, s), 2.50–3.20 (1H, b), 4.33 (2H, d), 6.00 (1H, s), 6.30–6.60 (2H, m).

REFERENCE EXAMPLE 4.

Compounds 4b and 4c as shown below in Table 2 were prepared in the same manner as in Reference Example 3.

TABLE 2

$$R_1\underset{N\diagdown O}{\overset{}{\diagup\hspace{-0.3em}\diagdown}}CH=\overset{R_3}{\underset{|}{C}}-CH_2OH \quad (4)$$

| Comp. No. | $R_1$ | Position of allyl alcohol | $R_3$ | Yield (%) | Form | $^1$H—NMR (CDCl$_3$) δ (ppm) |
|---|---|---|---|---|---|---|
| 4a | 3-$CH_3$ | 5 | H | 67.6 | oil | 2.30 (3H, s), 2.50–3.20 (1H, b), 4.33 (2H, d), 6.00 (1H, s), 6.30–6.60 (2H, m) |
| 4b | 5-$CH_3$ | 3 | H | 89.0 | oil | 2.35 (3H, s), 3.30–3.82 (1H, b), 4.28 (2H, d), 6.07 (1H, s), 6.38–6.60 (2H, m) |
| 4c | 3-$CH_3$ | 5 | $CH_3$ | 87.8 | oil | 2.00 (3H, s), 2.30 (3H, s), 2.70–3.30 (1H, b), 4.20 (2H, b,s), 6.00 (1H, s), 6.45 (1H, s) |

REFERENCE EXAMPLE 5

A 4.5 g quantity of 3-methyl-5-isoxazolyl-allyl alcohol was dissolved in 100 ml of dichloromethane. To the solution was added 8.5 g of pyridinium chlorochromate at room temperature and the mixture was stirred for 4 hours. After completion of the reaction, the organic layer was decanted and concentrated. The residue was purified by column chromatography using chlorform as an eluent, giving 3 g of 3-methyl-5-isoxazolyl-acrylaldehyde (Compound 2a) in a yield of 67.7%.

Elementary analysis ($C_7H_7NO_2$):

| | C | H | N |
|---|---|---|---|
| Calcd. (%) | 61.31 | 5.14 | 10.21 |
| Found (%) | 60.72 | 5.10 | 10.02 |

REFERENCE EXAMPLE 6

Compounds 2b and 2c as shown below in Table 3 were prepared in the same manner as in Reference Example 5.

TABLE 3

$$R_1\underset{N\diagdown O}{\overset{}{\diagup\hspace{-0.3em}\diagdown}}CH=\overset{R_3}{\underset{|}{C}}-CHO \quad (2)$$

| Comp. No. | $R_1$ | Position of acrylaldehyde | $R_3$ | Yield (%) | mp (°C.) | Molecular formula |
|---|---|---|---|---|---|---|
| 2a | 3-$CH_3$ | 5 | H | 67.7 | 66–68 | $C_7H_7NO_2$ |
| 2b | 5-$CH_3$ | 3 | H | 76.1 | 105–106 | $C_7H_7NO_2$ |
| 2c | 3-$CH_3$ | 5 | $CH_3$ | 73.2 | 95–97 | $C_8H_9NO_2$ |

EXAMPLE 1

To 5 ml of acetic acid were added 0.3 g of 3-methyl-5-isoxazolyl-acrylaldehyde, 0.35 g of rhodanine, 0.2 g of sodium acetate and 0.8 ml of acetic anhydride. The mixture was refluxed with heating for 2 hours. After completion of the reaction, the reaction mixture was cooled and the precipitate was separated by filtration. The solids were washed and recrystallized from acetic acid, giving 0.3 g of 5-[3-(3-methyl-5-isoxazolyl)-1,3-propanediene]rhodanine (Compound 1a) having a melting point of 250° to 251° C. in a yield of 54.5%. MS, m/e :252 (M+).

Elementary analysis (for $C_{10}H_8N_2O_2S_2 \cdot 1/2H_2O$):

| | C | H | N |
|---|---|---|---|
| Calcd. (%) | 45.96 | 3.09 | 10.72 |
| Found (%) | 45.99 | 3.13 | 10.32 |

EXAMPLE 2

Using an appropriate starting material, Compounds 1b-1f as shown below in Table 4 were prepared in the same manner as in Example 1.

TABLE 4

$$\text{(structure: } R_1\text{-isoxazole-CH=C(R_3)-CH=(rhodanine with N-R_2, S, S, O)}\text{)} \quad (1)$$

| Comp. No. | $R_1$ | Position of vinyl | $R_3$ | $R_2$ | Yield (%) | mp (°C.) | MS (M+) | Molecular formula |
|---|---|---|---|---|---|---|---|---|
| 1a | 3-$CH_3$ | 5 | H | H | 54.5 | 250–251 | 252 | $C_{10}H_8N_2O_2S_2\cdot\frac{1}{2}H_2O$ |
| 1b | 3-$CH_3$ | 5 | H | $CH_2CO_2H$ | 60.8 | 241–242 | 310 | $C_{12}H_{10}N_2O_4S_2\cdot CH_3CO_2H$ |
| 1c | 3-$CH_3$ | 5 | H | $CH_2CH_2CO_2H$ | 67.8 | 232–234 | 324 | $C_{13}H_{12}N_2O_4S_2$ |
| 1d | 5-$CH_3$ | 3 | H | $CH_2CO_2H$ | 58.8 | 231–232 | 310 | $C_{12}H_{10}N_2O_4S_2$ |
| 1e | 3-$CH_3$ | 5 | $CH_3$ | $CH_2CO_2H$ | 58.1 | >300 | 324 | $C_{13}H_{12}N_2O_4S_2\cdot\frac{1}{2}H_2O$ |
| 1f | 3-$CH_3$ | 5 | $CH_3$ | $CH_2CH_2CO_2H$ | 40.6 | 235–236 | 338 | $C_{14}H_{14}N_2O_4S_2$ |

EXAMPLE 3

(a) A 3.2 g quantity of 3-methyl-5-isoxazolylaldehyde, 5.6 g of rhodanine-3-acetic acid and 2.9 g of sodium acetate were added to 30 ml of acetic anhydride and the mixture was stirred with heating at 130° to 150° C. for 30 minutes and poured into ice water. The precipitate was separated by filtration and recrystallized from dimethylformamide, giving 4.0 g of 5-(3-methyl-5-isoxazolylmethylene)rhodanine-3acetic acid having a melting point of 280° to 283° C. (decomposition) in a yield of 48.8%.

Elementary analysis (for $C_{10}H_8N_2O_4S_2\cdot H_2O$):

|  | C | H | N |
|---|---|---|---|
| Calcd. (%) | 39.72 | 3.33 | 9.27 |
| Found (%) | 39.08 | 3.24 | 8.88 |

(b) In 100 ml of water were dissolved 2.0 g of 5-(3-methyl-5-isoxazolylmethylene)rhodanine-3-acetic acid and 1.0 g of sodium hydrogencarbonate. To the solution was added 1.0 g of 10% palladium charcoal and the mixture was subjected to a reduction at room temperature and under a hydrogen pressure of 3 atm. After completion of the reaction, the catalyst was removed by filtration. To the filtrate was added dilute hydrochloric acid to adjust the pH to 1. The precipitate was separated by filtration and recrystallized from water, giving 0.6 g of 5-(3-methyl-5-isoxazolylmethyl)rhodanine-3-acetic acid (Compound 1g) having a melting point of 235° to 240° C. (decomposition) in a yield of 30%.

Elementary analysis (for $C_{10}H_{10}N_2O_4S_2$):

|  | C | H | N |
|---|---|---|---|
| Calcd. (%) | 41.95 | 3.52 | 9.78 |
| Found (%) | 41.33 | 3.25 | 9.57 |

EXAMPLE 4

Compounds 1h to 1i as shown below in Table 5 were prepared in the same manner as in Example 3.

TABLE 5

| Comp. No. | $R_1$ | Position of methylene | $R_2$ | Yield (%) | mp (°C.) | Elementary analysis (%) |
|---|---|---|---|---|---|---|
| 1g | 3-$CH_3$ | 5 | —$CH_2COOH$ | 30 | 235–240 (decomp.) | for $C_{10}H_{10}N_2O_4S_2$<br>　　C　　H　　N<br>Calcd. 41.95 3.52 9.78<br>Found 41.33 3.25 9.57 |
| 1h | 3-$CH_3$ | 5 | —$CH_2CH_2COOH$ | 30 | 229–231 (decomp.) | for $C_{11}H_{12}N_2O_4S_2$<br>　　C　　H　　N<br>Calcd. 43.99 4.03 9.33<br>Found 43.85 3.66 9.10 |
| 1i | 5-$CH_3$ | 3 | —$CH_2COOH$ | 15 | 285–290 (decomp.) | for $C_{10}H_{10}N_2O_4S_2$<br>　　C　　H　　N<br>Calcd. 41.95 3.52 9.78<br>Found 42.37 3.21 9.63 |

Given below are examples of pharmaceutical compositions prepared by using the compounds of the present invention.

Preparation 1: Tablets

Tablets were prepared from the following composition (300 mg per tablet).

| | |
|---|---|
| Compound 1b | 100 mg |
| Lactose | 47 mg |
| Corn starch | 50 mg |
| Crystalline cellulose | 50 mg |
| Hydroxypropyl cellulose | 15 mg |
| Talc | 2 mg |
| Magnesium stearate | 2 mg |
| Ethyl cellulose | 30 mg |
| Fatty acid glyceride | 2 mg |
| Titanium dioxide | 2 mg |
| Total: | 300 mg |

Preparation 2: Capsules

An encapsulated preparation was formulated from the following composition (200 mg per capsule).

| Compound 1g | 50 mg |
|---|---|
| Lactose | 50 mg |
| Corn starch | 47 mg |
| Crystalline cellulose | 50 mg |
| Talc | 2 mg |
| Magnesium stearate | 1 mg |
| Total: | 200 mg |

Pharmacological Test

Aldose reductase inhibitory activity

Rat Lens Aldose Reductase:

This test was conducted according to the method described in J. Biol. Chem., 240, 877 (1965).

Sprague-Dawley rats weighing 100 to 150 g were suffocated with carbon dioxide and the lenses were carefully removed. The lenses were then homogenized in cold distilled water (0.4 ml/lens) and the homogenate was centrifuged at 10,000 rpm for 10 min. The enzyme, i.e. aldose reductase was spectrophotometrically measured by following the decrease in NADPH at 340 nm with glyceraldehyde as substrate. An $IC_{50}$ i.e., a concentration of the test compound at which 50% inhibition of aldose reductase is achieved was calculated from estimated dose-response curves. Table 6 below shows the results.

TABLE 6

| Compound | $IC_{50}$ ($\times 10^{-6}$ Mole) |
|---|---|
| 1a | 4.0 |
| 1b | 0.13 |
| 1g | 0.64 |

We claim:

1. A rhodanine derivative represented by the formula

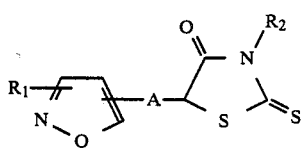

wherein $R_1$ is lower alkyl, A is a group of the formula

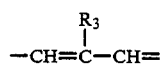

(in which $R_3$ is hydrogen or lower alkyl) or methylene, and $R_2$ is hydrogen or a group of the formula $-(CH_2)_n COOH$ (in which n is an integer of 1 to 6) or a salt thereof 2. A compound according to claim 1 which is represented by the formula

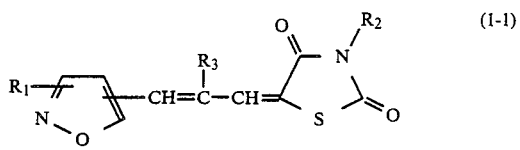

wherein $R_1$ is lower alkyl, $R_2$ is hydrogen or a group of the formula $-(CH_2)_n COOH$ (in which n is an integer of 1 to 6) and $R_3$ is hydrogen or lower alkyl.

3. A compound according to claim 1 which is represented by the formula

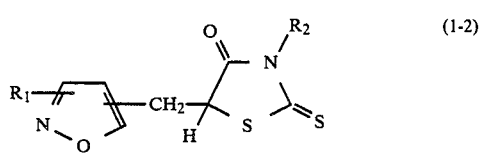

wherein $R_1$ is lower alkyl and $R_2$ is a group of the formula $-(CH_2)_n COOH$ wherein n is an integer of 1 to 6.

4. A compound according to claim 1 which is represented by the formula

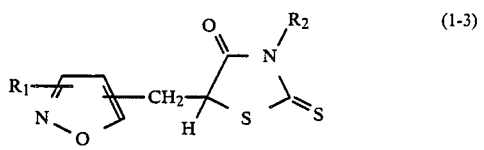

wherein $R_1$ is lower alkyl and $R_2$ is a group of the formula $-(CH_2)_n COOH$ wherein n is an integer of 1.

5. A compound according to claim 1 which is 5[3-(3-methyl-5-isoxazolyl)1,3-propanediene]-rhodanine.

6. A compound according to claim 1 which is 5-[3-(3-methyl-5-isoxazolyl)-1,3-propandiene]-3-carboxymethylrhodanine.

7. A compound according to claim 1 which is 5-[3-(5-methyl-3-isoxazolyl)-1,3-propandiene]3-carboxymethylrhodanine.

8. A compound according to claim 1 which is 5[3-(3-methyl-5-isoxazolyl)-2-methyl-1,3-propandiene]-3-carboxymethylrhodanine.

9. A compound according to claim 1 which is 5-(3-methyl-5-isoxazolylmethyl)-3-carboxymethylrhodanine.

* * * * *